US010219835B2

(12) United States Patent
Shluzas

(10) Patent No.: US 10,219,835 B2
(45) Date of Patent: *Mar. 5, 2019

(54) SYSTEMS AND DEVICES FOR CONNECTING A LONGITUDINAL MEMBER TO A BONE PORTION

(71) Applicant: Zimmer Spine, Inc., Edina, MN (US)

(72) Inventor: Alan E. Shluzas, Redwood City, CA (US)

(73) Assignee: Zimmer Spine, Inc., Edina, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/821,309

(22) Filed: Nov. 22, 2017

(65) Prior Publication Data
US 2018/0092664 A1    Apr. 5, 2018

Related U.S. Application Data

(63) Continuation of application No. 14/812,862, filed on Jul. 29, 2015, now Pat. No. 9,848,913, which is a
(Continued)

(51) Int. Cl.
A61B 17/70    (2006.01)
A61B 17/86    (2006.01)
A61B 17/00    (2006.01)

(52) U.S. Cl.
CPC ...... A61B 17/7002 (2013.01); A61B 17/7035 (2013.01); A61B 17/7037 (2013.01);
(Continued)

(58) Field of Classification Search
CPC ............ A61B 17/7002; A61B 17/7032; A61B 17/7035; A61B 17/7037; A61B 17/8605
See application file for complete search history.

(56) References Cited

U.S. PATENT DOCUMENTS 2,746,506 A    5/1956    Poupitch
5,005,562 A    4/1991    Cotrel
(Continued)

FOREIGN PATENT DOCUMENTS

WO    WO-03068083 A1    8/2003

OTHER PUBLICATIONS

"U.S. Appl. No. 10/075,668, Examiner Interview Summary dated Feb. 24, 2005", 3 pgs.
(Continued)

Primary Examiner — Anu Ramana
(74) Attorney, Agent, or Firm — Schwegman Lundberg & Woessner, P.A.

(57) ABSTRACT

An apparatus (10) includes a fastener (16) engageable with a bone portion to connect a longitudinal member (12) to the bone portion. A housing (40) has a first passage (42) configured to receive the longitudinal member (12) and a second passage (44) extending transverse to the first passage. The fastener (16) extends through an opening (50) in the housing (40) into the second passage (44). A longitudinal axis (18) of the fastener (16) is positionable in any one of a plurality of angular positions relative to a longitudinal axis (46) of the second passage (44). A spacer (60) received in the second passage (44) of the housing (40) is engageable with the fastener (16) and the longitudinal member (12). A member (70) applies a force to prevent relative movement between the fastener (16) and the housing (40) and permit manual movement of the fastener (16) relative to the housing (40) against the force when the longitudinal member (12) is disengaged from the spacer (60). A clamping mechanism (90) clamps the longitudinal member (12), the spacer (60), and the housing (40) to the fastener (16) to prevent movement of the fastener relative to the housing.

17 Claims, 3 Drawing Sheets

Related U.S. Application Data continuation of application No. 14/262,925, filed on Apr. 28, 2014, now abandoned, which is a continuation of application No. 13/013,257, filed on Jan. 25, 2011, now Pat. No. 8,709,050, which is a continuation of application No. 11/415,676, filed on May 2, 2006, now Pat. No. 7,879,075, which is a continuation of application No. 10/075,668, filed on Feb. 13, 2002, now Pat. No. 7,066,937.

(52) U.S. Cl.
CPC ...... *A61B 17/8605* (2013.01); *A61B 17/7032* (2013.01); *A61B 2017/00526* (2013.01); *Y10T 29/49828* (2015.01); *Y10T 29/49947* (2015.01)

(56) References Cited

U.S. PATENT DOCUMENTS

| | | | |
|---|---|---|---|
| 5,135,489 A | 8/1992 | Jepson et al. |
| 5,207,678 A | 5/1993 | Harms et al. |
| 5,443,467 A | 8/1995 | Biedermann et al. |
| 5,466,237 A | 11/1995 | Byrd, III et al. |
| 5,474,555 A | 12/1995 | Puno et al. |
| 5,476,464 A | 12/1995 | Metz-stavenhagen et al. |
| 5,496,142 A | 3/1996 | Fodor |
| 5,584,834 A | 12/1996 | Errico et al. |
| 5,613,968 A | 3/1997 | Lin |
| 5,639,074 A | 6/1997 | Greenhill et al. |
| 5,669,911 A | 9/1997 | Errico et al. |
| 5,672,176 A | 9/1997 | Biedermann |
| 5,690,630 A | 11/1997 | Errico et al. |
| 5,733,285 A | 3/1998 | Errico et al. |
| 5,797,911 A | 8/1998 | Sherman et al. |
| 5,817,094 A | 10/1998 | Errico et al. |
| 5,876,402 A | 3/1999 | Errico et al. |
| 5,879,350 A | 3/1999 | Sherman et al. |
| 5,885,286 A | 3/1999 | Sherman et al. |
| 6,010,503 A | 1/2000 | Richelsoph et al. |
| 6,022,350 A | 2/2000 | Ganem |
| 6,063,090 A | 5/2000 | Schlapfer |
| 6,074,391 A | 6/2000 | Metz-stavenhagen et al. |
| 6,077,262 A | 6/2000 | Schlapfer et al. |
| 6,090,110 A | 7/2000 | Metz-stavenhagen |
| 6,090,111 A | 7/2000 | Nichols |
| 6,113,601 A | 9/2000 | Tatar |
| 6,139,550 A | 10/2000 | Michelson |
| 6,238,396 B1 | 5/2001 | Lombardo |
| 6,248,105 B1 | 6/2001 | Schlapfer et al. |
| 6,261,287 B1 | 7/2001 | Metz-Stavenhagen |
| 6,280,442 B1 | 8/2001 | Barker et al. |
| 6,287,311 B1 | 9/2001 | Sherman et al. |
| 6,296,642 B1 | 10/2001 | Morrison et al. |
| 6,302,888 B1 | 10/2001 | Mellinger et al. |
| 6,375,657 B1 | 4/2002 | Doubler et al. |
| 6,402,752 B2 | 6/2002 | Schäffler-Wachter et al. |
| 6,440,137 B1 | 8/2002 | Horvath et al. |
| 6,454,768 B1 | 9/2002 | Jackson |
| 6,471,705 B1 | 10/2002 | Biedermann et al. |
| 6,485,491 B1 | 11/2002 | Farris et al. |
| 6,488,681 B2 | 12/2002 | Martin et al. |
| 6,511,099 B2 | 1/2003 | Bartholomä et al. |
| 6,530,929 B1 | 3/2003 | Justis et al. |
| 6,537,276 B2 | 3/2003 | Metz-Stavenhagen |
| 6,540,748 B2 | 4/2003 | Lombardo |
| 6,547,725 B1 | 4/2003 | Paolitto et al. |
| 6,551,323 B2 | 4/2003 | Doubler et al. |
| 6,565,565 B1 | 5/2003 | Yuan et al. |
| 6,565,567 B1 | 5/2003 | Haider |
| 6,585,740 B2 | 7/2003 | Schlapfer et al. |
| 6,726,687 B2 | 4/2004 | Jackson |
| 6,755,829 B1 | 6/2004 | Bono et al. |
| 6,835,196 B2 | 12/2004 | Biedermann et al. |
| 6,837,889 B2 | 1/2005 | Shluzas |
| 6,869,433 B2 | 3/2005 | Glascott |
| 6,905,500 B2 | 6/2005 | Jeon et al. |
| 7,018,378 B2 | 3/2006 | Biedermann et al. |
| 7,066,937 B2 | 6/2006 | Shluzas |
| 7,087,057 B2 | 8/2006 | Konieczynski et al. |
| 7,144,396 B2 | 12/2006 | Shluzas |
| 7,604,656 B2 | 10/2009 | Shluzas |
| 7,879,075 B2 | 2/2011 | Shluzas |
| 8,709,050 B2 | 4/2014 | Shluzas |
| 8,936,624 B2 | 1/2015 | Shluzas |
| 9,848,913 B2 | 12/2017 | Shluzas |
| 2001/0001119 A1 | 5/2001 | Lombardo |
| 2002/0091386 A1 | 7/2002 | Martin et al. |
| 2002/0138076 A1 | 9/2002 | Biedermann et al. |
| 2003/0004512 A1 | 1/2003 | Farris et al. |
| 2004/0153068 A1 | 8/2004 | Janowski et al. |
| 2004/0176766 A1 | 9/2004 | Shluzas et al. |
| 2006/0293665 A1 | 12/2006 | Shluzas |
| 2010/0125302 A1 | 5/2010 | Hammill et al. |
| 2014/0228889 A1 | 8/2014 | Shluzas |
| 2015/0327888 A1 | 11/2015 | Shluzas |

OTHER PUBLICATIONS

"U.S. Appl. No. 10/075,668, Final Office Action dated Jun. 10, 2004", 6 pgs.
"U.S. Appl. No. 10/075,668, Final Office Action dated Aug. 25, 2005", 5 pgs.
"U.S. Appl. No. 10/075,668, Non Final Office Action dated Mar. 5, 2003", 5 pgs.
"U.S. Appl. No. 10/075,668, Non Final Office Action dated Aug. 26, 2004", 6 pgs.
"U.S. Appl. No. 10/075,668, Non Final Office Action dated Nov. 26, 2003", 5 pgs.
"U.S. Appl. No. 10/075,668, Notice of Allowance dated Nov. 23, 2005", 9 pgs.
"U.S. Appl. No. 10/075,668, Response filed Feb. 28, 2005 to Non Final Office Action dated Aug. 26, 2004", 17 pgs.
"U.S. Appl. No. 10/075,668, Response filed Mar. 15, 2004 to Non Final Office Action dated Nov. 26, 2003", 29 pgs.
"U.S. Appl. No. 10/075,668, Response filed Jun. 9, 2005 to Non Final Office Action dated Aug. 26, 2004", 19 pgs.
"U.S. Appl. No. 10/075,668, Response filed Jul. 22, 2004 to Final Office Action dated Jun. 10, 2004", 49 pgs.
"U.S. Appl. No. 10/075,668, Response filed Sep. 2, 2003 to Non Final Office Action dated Mar. 5, 2003", 19 pgs.
"U.S. Appl. No. 10/075,668, Response filed Oct. 25, 2005 to Final Office Action dated Aug. 25, 2005", 11 pgs.
"U.S. Appl. No. 10/075,668, Supplemental Amendment filed Mar. 24, 2005", 2 pgs.
"U.S. Appl. No. 10/075,668, Supplemental Notice of Allowability dated Jan. 19, 2006", 5 pgs.
"U.S. Appl. No. 11/415,676, Applicant's Summary of Examiner Interview filed Oct. 15, 2010", 1 pg.
"U.S. Appl. No. 11/415,676, Final Office Action dated Jul. 16, 2010", 7 pgs.
"U.S. Appl. No. 11/415,676, Non Final Office Action dated Feb. 3, 2010", 4 pgs.
"U.S. Appl. No. 11/415,676, Notice of Allowance dated Sep. 27, 2010", 8 pgs.
"U.S. Appl. No. 11/415,676, Preliminary Amendment filed May 2, 2006", 7 pgs.
"U.S. Appl. No. 11/415,676, Response filed Apr. 29, 2010 to Non Final Office Action dated Feb. 3, 2010", 8 pgs.
"U.S. Appl. No. 11/415,676, Response filed Sep. 16, 2010 to Final Office Action dated Jul. 16, 2010", 9 pgs.
"U.S. Appl. No. 13/013,257, 312 Amendment filed Nov. 19, 2013", 7 pgs.
"U.S. Appl. No. 13/013,257, Final Office Action dated May 8, 2013", 8 pgs.
"U.S. Appl. No. 13/013,257, Non Final Office Action dated Dec. 19, 2012", 8 pgs.
"U.S. Appl. No. 13/013,257, Notice of Allowance dated Aug. 22, 2013", 10 pgs.

(56) References Cited

OTHER PUBLICATIONS

"U.S. Appl. No. 13/013,257, Notice of Allowance dated Dec. 9, 2013", 11 pgs.

"U.S. Appl. No. 13/013,257, Response filed Mar. 13, 2013 to Non Final Office Action dated Dec. 19, 2012", 9 pgs.

"U.S. Appl. No. 13/013,257, Response filed Aug. 8, 2013 to Final Office Action dated May 8, 2013", 10 pgs.

"U.S. Appl. No. 14/262,925, Decision on Pre-Appeal Brief dated Jul. 7, 2015", 2 pgs.

"U.S. Appl. No. 14/262,925, Final Office Action dated Mar. 27, 2015", 7 pgs.

"U.S. Appl. No. 14/262,925, Non Final Office Action dated Oct. 6, 2014", 8 pgs.

"U.S. Appl. No. 14/262,925, Pre-Brief Conference request filed May 26, 2015", 6 pgs.

"U.S. Appl. No. 14/262,925, Response filed Jan. 6, 2015 to Non Final Office Action dated Oct. 6, 2014", 11 pgs.

"U.S. Appl. No. 14/445,552, Examiner Interview Summary dated Oct. 30, 2014", 3 pgs.

"U.S. Appl. No. 14/445,552, Non Final Office Action dated Oct. 7, 2014", 9 pgs.

"U.S. Appl. No. 14/445,552, Notice of Allowance dated Nov. 26, 2014", 8 pgs.

"U.S. Appl. No. 14/445,552, Response filed Nov. 4, 2014 to Non Final Office Action dated Oct. 7, 2014", 12 pgs.

"U.S. Appl. No. 14/812,862, Final Office Action dated Apr. 26, 2017", 7 pgs.

"U.S. Appl. No. 14/812,862, Final Office Action dated Sep. 12, 2016", 6 pgs.

"U.S. Appl. No. 14/812,862, Non Final Office Action dated May 19, 2016", 8 pgs.

"U.S. Appl. No. 14/812,862, Notice of Allowance dated Aug. 24, 2017", 8 pgs.

"U.S. Appl. No. 14/812,862, Response filed Jul. 26, 2017 to Final Office Aciton dated Apr. 26, 2017", 17 pgs.

"U.S. Appl. No. 14/812,862, Response filed Aug. 19, 2016 to Non Final Office Action dated May 19, 2016", 13 pgs.

"Speed Security and Simplicity in Harmony, Expedium Spine System", DePuySpine, (Aug. 2004), 6 pgs.

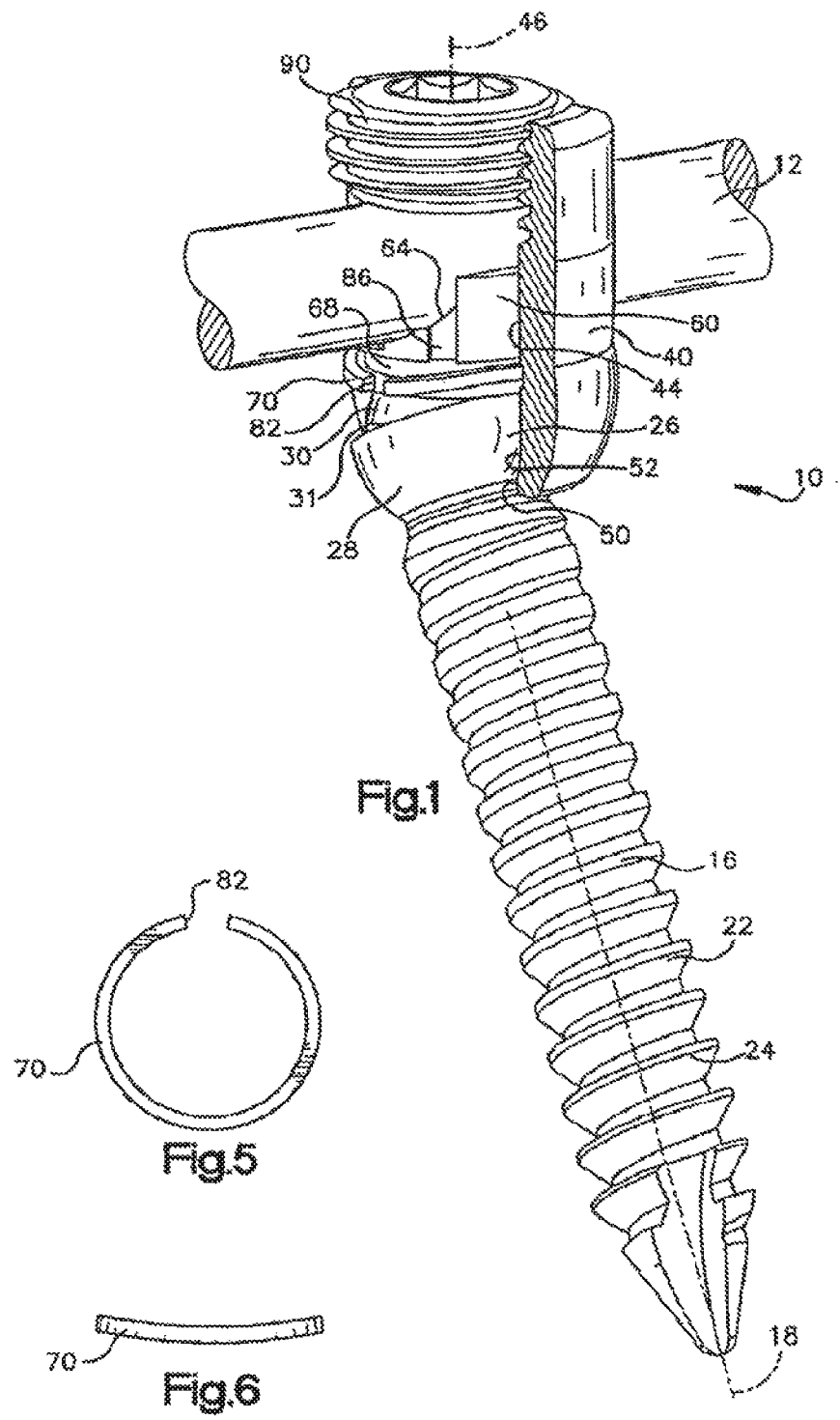

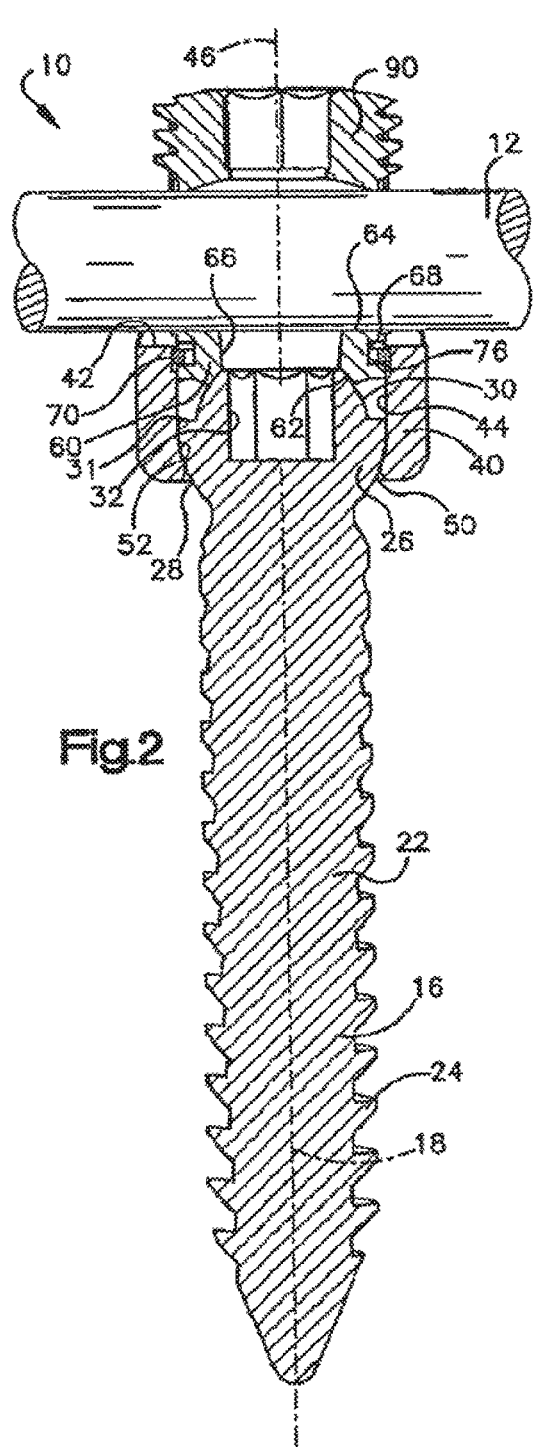
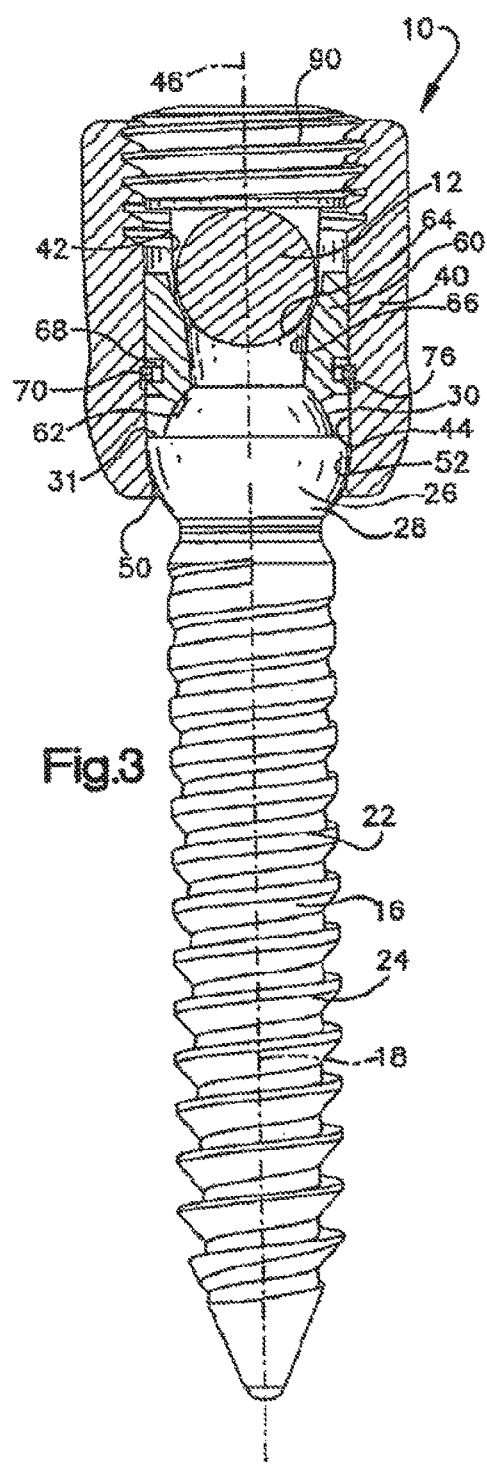

SYSTEMS AND DEVICES FOR CONNECTING A LONGITUDINAL MEMBER TO A BONE PORTION

CROSS-REFERENCE TO RELATED APPLICATION

This application is a continuation of U.S. application Ser. No. 14/262,925, filed Apr. 28, 2014, now abandoned, which is a continuation of U.S. application Ser. No. 13/013,257, filed Jan. 25, 2011, now U.S. Pat. No. 8,709,050, which is a continuation of U.S. application Ser. No. 11/415,676, filed May 2, 2006, now U.S. Pat. No. 7,879,075, which is a continuation of U.S. application Ser. No. 10/075,668, filed Feb. 13, 2002, now U.S. Pat. No. 7,066,937, the disclosures of which are incorporated by reference herein in their entirety.

TECHNICAL FIELD

The present invention relates to an apparatus which is used to retain bone portions, such as vertebrae of a spinal column, in a desired spatial relationship.

BACKGROUND OF THE INVENTION

A known apparatus for retaining vertebrae of a spinal column in a desired spatial relationship is disclosed in U.S. Pat. No. 6,280,442. U.S. Pat. No. 6,280,442 discloses an apparatus including a longitudinal member extendable along the spinal column. A fastener engageable with a vertebra of the spinal column connects the longitudinal member to the vertebra. A housing has a first passage through which the longitudinal member extends and a second passage with a longitudinal axis extending transverse to the first passage. The fastener extends through an opening in the housing into the second passage. The longitudinal axis of the fastener is positionable in any one of a plurality of angular positions relative to the longitudinal axis of the second passage.

A spacer received in the housing is engageable with the fastener and the longitudinal member. A clamping member threadably engages the housing to clamp the longitudinal member, the spacer, and the housing to the fastener to prevent movement of the fastener relative to the housing. When the longitudinal member is disengaged from the spacer, the housing may not remain in position relative to the fastener until the longitudinal member is clamped to the spacer. Accordingly, the housing must be held in position relative to the fastener by a surgeon while the longitudinal member is clamped to the spacer.

SUMMARY OF THE INVENTION

The present invention is an apparatus which is used to retain bone portions in a desired spatial relationship. The apparatus includes a longitudinal member connectable with a bone portion. A fastener having a longitudinal axis is engageable with the bone portion to connect the longitudinal member to the bone portion. A housing has a first passage configured to receive the longitudinal member. The housing has a second passage with a longitudinal axis extending transverse to the first passage. The fastener extends through an opening in the housing into the second passage and is movable relative to the housing. The longitudinal axis of the fastener is positionable in any one of a plurality of angular positions relative to the longitudinal axis of the second passage.

A spacer received in the second passage of the housing is engageable with the fastener and the longitudinal member. A member applies a force to prevent relative movement between the fastener and the housing when the longitudinal member is disengaged from the spacer and the spacer engages the fastener. The fastener and the housing are manually movable relative to each other against the force when the longitudinal member is disengaged from the spacer and the member applies the force. A clamping mechanism clamps the longitudinal member, the spacer, and the housing to the fastener to prevent movement of the fastener relative to the housing. Accordingly, the housing and the fastener can be positioned relative to each other and the member will hold the fastener and the housing in the relative positions before the longitudinal member is connected to the housing.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein:

FIG. 1 is a perspective view of an apparatus constructed in accordance with the present invention with portions removed for clarity;

FIG. 2 is a sectional view of the apparatus of FIG. 1;

FIG. 3 is a part sectional view of the apparatus of FIG. 1;

FIG. 5 is a plan view of a spring member of the apparatus of FIG. 1; and FIG. 6 is a side view of the spring member.

DESCRIPTION OF THE INVENTION

Figure 4:
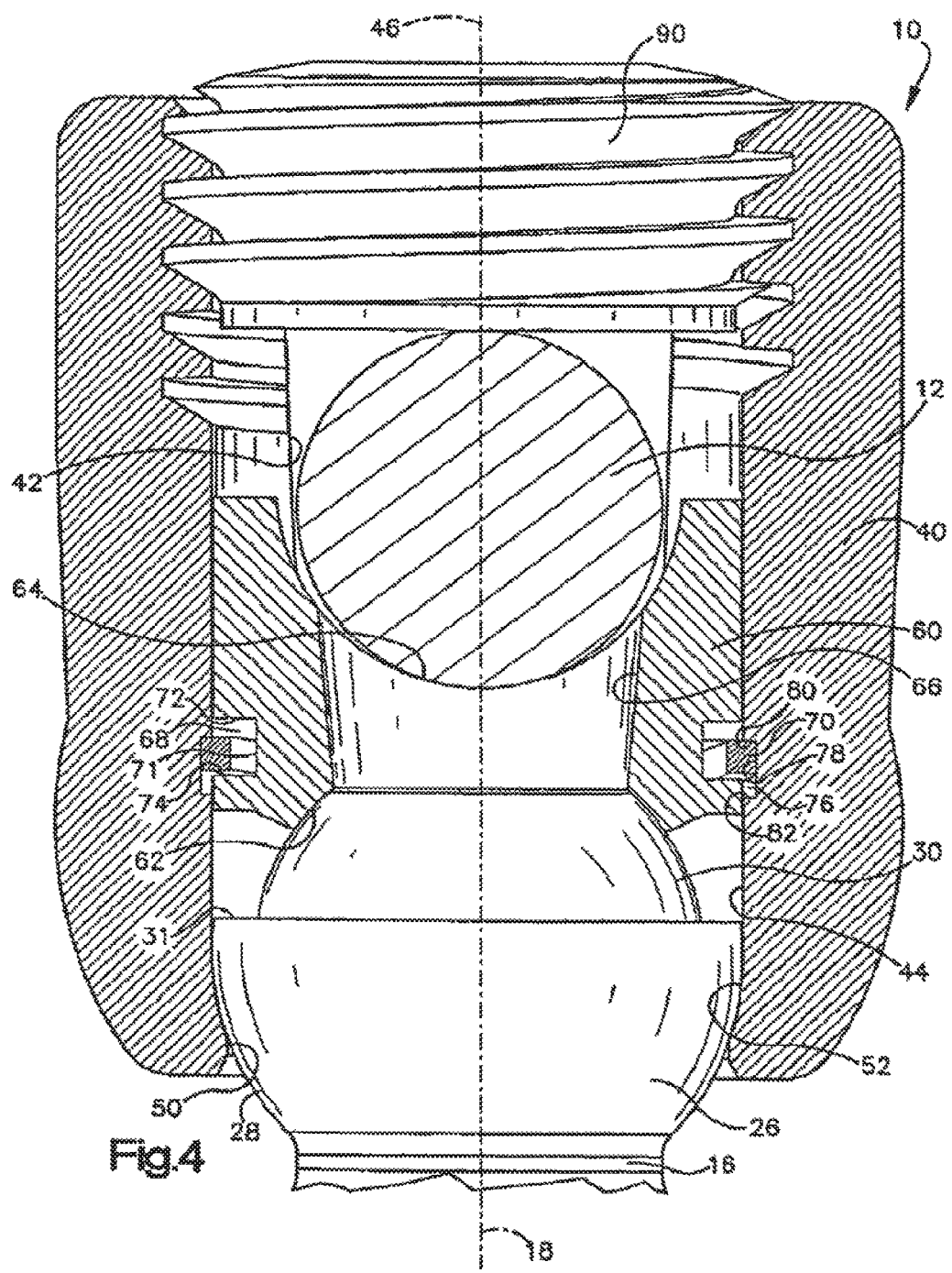
FIG. 4 is an enlarged sectional view of a portion of the apparatus of FIG. 1.

The present invention is directed to an apparatus for retaining bone portions, such as vertebrae of a spinal column, in a desired spatial relationship. FIGS. 1-4 illustrate an apparatus 10 constructed according to the present invention. The apparatus 10 includes a surgically implantable longitudinal member or rod 12 for maintaining bone portions, such as vertebrae of a spinal column, in a desired spatial relationship. The member 12 is connected with vertebrae of the spinal column by fasteners 16.

The rod 12 is made of a suitable biocompatible material and has a length which is at least sufficient to enable the rod to span at least two vertebrae. Of course, the length of the rod 12 in any particular installation will depend upon the condition to be corrected and the number of vertebrae to be held in a desired spatial relationship relative to each other by the rod.

The rod 12 (FIGS. 1-3) is connected to a respective vertebra by the fastener 16 made of a suitable biocompatible material. The fastener 16 has a longitudinal axis 18 and a threaded end portion 22 having a course thread convolution 24 which engages the vertebra. A second end portion 26 of the fastener 16 is provided with a first part spherical surface 28. The second end portion 26 of the fastener 16 also includes a second part spherical surface 30 having a diameter less than a diameter of the first part spherical surface 28. As can be seen in FIG. 3, the first part spherical surface 28 extends over a longer arc length, oriented in a cross-section taken along longitudinal axis 46, than the second part spherical surface 30. Additionally, first part spherical surface 28 encompasses a larger surface area than the second part spherical surface 30 as a result of having a larger diameter and having a larger arc length. A radially extending shoulder 31 extends between the part spherical surfaces 28 and 30. A recess 32 (FIG. 2) is provided on the end portion 26 of the fastener 16. The recess 32 receives a tool (not shown) that applies torque to the fastener 16 to turn the thread convolution 24 into the vertebra.

The fastener 16 (FIGS. 1-4) extends into a housing 40 that interconnects the rod 12 and the fastener 16. The housing 40 (FIG. 2) has a first passage 42 through which the rod 12 extends. The housing 40 has a second passage 44 with a longitudinal axis 46 that extends transverse to the first passage 42. The fastener 16 extends through an opening 50 in the housing 40 and into the second passage 44. The first part spherical surface 28 of the fastener 16 engages a concave part spherical surface 52 of the housing 40. Accordingly, the fastener 16 is universally pivotable relative to the housing 40 so that the longitudinal axis 18 of the fastener 16 is positionable in any one of a plurality of angular positions relative to the longitudinal axis 46 of the passage 44.

A spacer 60 is housed in the second passage 44 of the housing 40. The spacer 60 (FIGS. 2-4) has a concave part spherical surface 62 that engages the part spherical surface 30 of the fastener 16. The shoulder 31 on the fastener 16 is engageable with the spacer 60 to limit the relative movement between the fastener and the housing 40. The spacer 60 also has a concave part cylindrical surface 64 that engages the rod 12. The spacer 60 has an opening 66 through which the tool (not shown) extends to engage the recess 32 in the fastener 16. The tool extends through the opening 66 to apply torque to the fastener 16 and connect the fastener to the vertebra.

The spacer 60 (FIG. 4) has a circumferential groove 68 for receiving a compressible member such as a spring member 70. The groove 68 is defined by an axially extending cylindrical surface 71. An upper surface 72 extends radially outward from the cylindrical surface 71. A lower surface 74 extends radially outward from the cylindrical surface 71 and generally parallel to the upper surface 72.

The housing 40 includes a circumferential groove 76 for receiving the spring member 70 so that the spring member extends from the groove 68 in the spacer 60 to the groove in the housing. The groove 76 is defined by an axially extending cylindrical surface 78. An upper surface 80 extends radially inward from the cylindrical surface 78. A lower surface 82 extends radially inward from the cylindrical surface 78 and generally parallel to the upper surface 80.

The spring member 70 (FIGS. 5 and 6) is a ring having a gap 82. The gap 82 permits the spring member 70 to radially contract and expand. The spring member 70 has an arched shape, as viewed in FIG. 6, when the spring member 70 is disengaged from the spacer 60 and the housing 40. When the spring member 70 is received in the grooves 68 and 76 (FIG. 4), the spring member engages the lower surface 74 on the spacer 60 and the upper surface 80 on the housing 40.

The spring member 70 applies an axial force to the spacer 60 to prevent relative movement between the fastener 16 and the housing 40 when the rod 12 is disengaged from the spacer and the spacer engages the fastener. The spring member 70 urges the spacer 60 axially toward the fastener 16 and the part spherical surface 52 of the housing 40 against the part spherical surface 28 of the fastener. The part spherical surface 62 of the spacer 60 frictionally engages the part spherical surface 30 of the fastener 16 and the part spherical surface 28 of the fastener frictionally engages the part spherical surface 52 of the housing 40. The fastener 16 and the housing 40 are manually movable relative to each other by a surgeon when the rod 12 is disengaged from the spacer 60 and the spring member 70 applies the axial force. The force applied by the spring member 70 may be overcome by the surgeon to move the housing 40 relative to the fastener 16. Accordingly, the housing 40 can be positioned relative to the fastener 16 and held in position relative to the fastener by the spring member 70 without the rod 12 engaging the spacer 60. It is contemplated that any compressible member could be used to apply the force to the fastener 16 to prevent relative movement between the fastener and the housing 40 when the rod 12 is disengaged from the spacer 60.

The spacer 60 has four axially extending slots 86, one of which is shown in FIG. 1. The slots 86 intersect the groove 68. A tool (not shown) has four prongs that extend through the slots 86 and into engagement with the spring member 70. The tool grasps the spacer 60 and the spring member 70 for inserting the spacer and the spring member into the housing 40. The prongs of the tool engage the spring member 70 to radially contract the spring member into the groove 68 in the spacer 60. The prongs hold the spring member 70 in the radially contracted condition in the groove 68 while the spacer 60 and spring member are being inserted into the housing 40. Once the spacer 60 engages the fastener 16, the prongs are removed from the slots 86 and the spring member 70 radially expands into the groove 71 in the housing 40. Although the spacer 60 is described as having four slots 86, the spacer could have any number of slots and the tool would have the same number of prongs as the spacer has slots.

A clamping mechanism or set screw 90 (FIGS. 1-4) threadably engages the housing 40. The set screw 90 and the housing 40 have a German standard DIN513 buttress thread. It is contemplated that the set screw 90 and the housing 40 could have any desired thread formation. The set screw 90 engages and applies a force to the rod 12 to press the rod against the spacer 60 and the spacer against the fastener 16. The set screw 90 clamps the rod 12, the spacer 60, and the housing 40 to the fastener 16 to prevent movement of the fastener relative to the housing. The force applied by the set screw 90 cannot be overcome by the surgeon to move the housing 40 relative to the fastener 16.

The apparatus 10 is assembled by inserting the fastener 16 through the opening 50 in the housing 40 so that the part spherical surface 28 of the fastener engages the part spherical surface 52 of the housing. The spacer 60 and the spring member 70 are inserted into the housing 40 by radially compressing the spring member into the groove 68 in the spacer. The spacer 60 and the spring member 70 are inserted into the second passage 44 until the part spherical surface 62 of the spacer engages the part spherical surface 30 of the fastener 16. The spring member 70 is released and expands radially into the groove 76 in the housing 40.

A tool is inserted through the opening 66 in the spacer 60 and into the recess 32 in the fastener 16. Torque is applied to the fastener 16 to turn the thread convolution 24 into the vertebra. Once the fastener 16 is connected with the vertebra, the housing 40 can be positioned relative to the fastener. The spring member 70 maintains the position of the housing 40 relative to the fastener 16 while the rod 12 is disengaged from the spacer 60. Once the housing 40 is positioned relative to the fastener 16, the rod 12 is placed into the passage 42 and in engagement with the spacer 60. The set screw 90 is threaded into the housing 40 and into engagement with the rod 12. The set screw 90 clamps the rod 12, the spacer 60, and the housing 40 to the fastener 16 to prevent movement of the fastener relative to the housing. Alternatively, the fastener 16 may be connected to the vertebra prior to the spacer 60 and the spring member 70 being inserted into the housing 40.

From the above description of the invention, those skilled in the art will perceive improvements, changes and modifications. Such improvements, changes and modifications within the skill of the art are intended to be covered by the appended claims.

What is claimed:

1. A spinal fixation device, comprising:
   a fastener having:
      a shank; and
      a head comprising:
         a first spherical surface extending from a proximal end of the shank;
         a proximal surface;
         a second spherical surface extending from the proximal surface of the head; and
         a radially extending shoulder extending around a periphery of the head between the first and second spherical surfaces of the head, wherein the shoulder is disposed closer to the proximal surface of the head than the proximal end of the shank, along a longitudinal axis of the shank;
   a housing having a passage formed along a longitudinal axis thereof and adapted to seat the spherical surface of the head of the fastener;
   a spacer received in said passage of said housing and engageable with said head; and
   a compressible member disposed within the housing and positioned between the spacer and the housing, the compressible member generating a frictional force between the head and the housing to enable the shank to be maintained in a desired angular orientation relative to the housing in the absence of the spinal fixation element.

2. The device of claim 1, wherein the compressible member is positioned above the shoulder of the head.

3. The device of claim 1, wherein the compressible member is substantially C-shaped.

4. The device of claim 1, wherein the spacer has at least two slots aligned along the longitudinal axis of the housing, the slots extending distally from a proximal edge of the spacer.

5. The device of claim 1, wherein the compressible member exerts the frictional force on the head through the spacer.

6. The device of claim 5, wherein:
   the housing has a channel in an inner wall thereof configured to receive at least a portion of the compressible member; and
   the spacer has a circumferential groove in an outer wall thereof configured to receive at least a portion of the compressible member.

7. The device of claim 6, wherein the entire channel in the inner wall of the housing and the circumferential groove in the spacer are disposed below the bottom-most portion of a channel in the proximal surface of the spacer adapted to receive a spinal fixation element.

8. The device of claim 1, wherein the passage of the housing and the spacer mate at a cylindrical interface when the spacer is engaged with the head such that the spacer is rotatable within the passage.

9. The device of claim 1, wherein the first spherical surface is configured to engage the passage of the housing over a surface area that is greater than that of an engagement between the second spherical surface and the spacer.

10. A spinal fixation device, comprising:
    a fastener having:
       a shank extending along a longitudinal axis; and
       a head comprising:
          a proximal surface having a tool recess;
          a first spherical portion extending from the proximal surface in a distal direction, the first spherical portion having a first radius;
          a distal neck connected to the shank; and
          a second spherical portion extending from the distal neck in a proximal direction, the second spherical portion having a second radius larger than the first radius;
       wherein the first and second spherical portions are connected to each other along a radially extending surface that is closer to the proximal surface of the head than the distal neck of the head, along the longitudinal axis of the shank;
    a housing comprising:
       a transverse slot configured to receive a rod;
       a longitudinal passage configured to receive the head; and
       a first part spherical surface sized to engage the second spherical portion; and
    a spacer comprising:
       an upper portion configured to engage the longitudinal passage; and
       a second part spherical portion configured to engage the first spherical portion.

11. The spinal fixation device of claim 10, further comprising a compressible member disposed between the longitudinal passage of the housing and the upper portion of the spacer, the compressible member configured to exert a longitudinal force against the head through the spacer.

12. The spinal fixation device of claim 11, wherein:
    the housing has a channel on an inner surface thereof configured to receive at least a portion of the compressible member; and
    the spacer has a circumferential groove in an outer surface thereof configured to receive at least a portion of the compressible member.

13. The spinal fixation device of claim 11, wherein the compressible member is adapted to expand or contract in a radial direction.

14. The spinal fixation device of claim 10, wherein the spacer has at least two slots aligned along a longitudinal axis of the housing, the slots extending distally from a proximal edge of the spacer.

15. The spinal fixation device of claim 10, wherein the fastener further comprises a radially extending shoulder extending around a periphery of the head between the first and second spherical portions of the head.

16. The spinal fixation device of claim 10, wherein:
    the second part spherical portion engages the first spherical portion along a first interface extending along a first arc length oriented in a longitudinal cross-section taken along the longitudinal axis; and
    the first part spherical portion engages the second spherical portion along a second interface extending along a second arc length oriented in the longitudinal cross-section;
    wherein the second arc length is greater in length than the first arc length when the housing and the spacer are disposed concentrically about the longitudinal axis on the head.

17. The spinal fixation device of claim 10, wherein the upper portion of the spacer is rotatable against the longitudinal passage of the housing when the second part spherical portion is engaged with the first spherical portion.

* * * * *